US008718746B2

(12) United States Patent
Cohn et al.

(10) Patent No.: US 8,718,746 B2
(45) Date of Patent: May 6, 2014

(54) PERICARDIAL SPACE IMAGING FOR CARDIAC SUPPORT DEVICE IMPLANTATION

(75) Inventors: William E. Cohn, Houston, TX (US); Aaron J. Hjelle, Champlin, MN (US); Robert G. Walsh, Lakeville, MN (US); Kevin Paul Bassett, Farmington, MN (US)

(73) Assignee: Mardil, Inc., Plymouth, MN (US)

( * ) Notice: Subject to any disclaimer, the term of this patent is extended or adjusted under 35 U.S.C. 154(b) by 838 days.

(21) Appl. No.: 12/142,891

(22) Filed: Jun. 20, 2008

(65) Prior Publication Data
US 2008/0319255 A1    Dec. 25, 2008

Related U.S. Application Data

(60) Provisional application No. 60/936,594, filed on Jun. 21, 2007.

(51) Int. Cl.
*A61B 5/00* (2006.01)

(52) U.S. Cl.
USPC ............ 600/431; 600/407; 600/420; 600/424

(58) Field of Classification Search
USPC .................. 600/420, 424, 431, 458
See application file for complete search history.

(56) References Cited

U.S. PATENT DOCUMENTS

| | | |
|---|---|---|
| 5,702,343 A | 12/1997 | Alferness |
| 5,931,810 A * | 8/1999 | Grabek .......................... 604/506 |
| 6,123,662 A | 9/2000 | Alferness et al. |
| 6,293,906 B1 | 9/2001 | Vanden Hoek et al. |
| 6,482,146 B1 | 11/2002 | Alferness et al. |
| 6,692,458 B2 | 2/2004 | Forman et al. |
| 6,702,732 B1 | 3/2004 | Lau et al. |
| 6,730,016 B1 | 5/2004 | Cox et al. |
| 6,859,661 B2 * | 2/2005 | Tuke .............................. 600/424 |
| 6,902,522 B1 | 6/2005 | Walsh et al. |
| 6,951,534 B2 | 10/2005 | Girard et al. |
| 7,226,440 B2 | 6/2007 | Gelfand et al. |
| 7,641,608 B1 * | 1/2010 | Ruggio ........................... 600/37 |
| 7,922,648 B1 * | 4/2011 | Hou et al. ....................... 600/37 |
| 2002/0082469 A1 * | 6/2002 | Taheri ............................. 600/37 |
| 2002/0173784 A1 * | 11/2002 | Sliwa et al. ..................... 606/28 |
| 2006/0167334 A1 | 7/2006 | Anstadt et al. |
| 2007/0208215 A1 | 9/2007 | Hjelle et al. |
| 2007/0270654 A1 | 11/2007 | Pignato et al. |

OTHER PUBLICATIONS

Baek, S.H. et al., Augmentation of Intrapericardial Nitric Oxide Level by a Prolonged-Release Nitric Oxide Donor Reduces Luminal Narrowing After Porcine Coronary Angioplasty, Circulation, Jun. 11, 2002;105(23):2779-84.

(Continued)

*Primary Examiner* — Peter Luong
(74) *Attorney, Agent, or Firm* — Gordon & Rees LLP

(57) ABSTRACT

A method for implanting a cardiac support device (CSD) on a patient's heart. An amount of contrast agent sufficient to cause structures on the heart to be visible upon fluoroscopic or other imaging is introduced into the pericardial space surrounding the heart. The heart and contrast agent are imaged to provide a visual indication of the location of the structures of the heart. The CSD is placed on the heart using the visual indications provided by the imaging.

4 Claims, 3 Drawing Sheets

(56) References Cited

OTHER PUBLICATIONS

Verrier, R.L. et al., Transatrial Access to the Normal Pericardial Space: A Novel Approach for Diagnostic Sampling, Pericardiocentesis, and Therapeutic Interventions, Circulation, Nov. 24, 1998;98(21):2331-3.

International Search Report and Written Opinion issued in US/PCT2008/067593, mailed Sep. 29, 2008, 8 pages.

* cited by examiner

PERICARDIAL SPACE IMAGING FOR CARDIAC SUPPORT DEVICE IMPLANTATION

REFERENCE TO RELATED APPLICATION

This application claims the benefit of U.S. Provisional Application Ser. No. 60/936,594 filed on Jun. 21, 2007, and entitled "Pericardial Space Imaging For Cardiac Support Device Implantation," which is incorporated herein by reference in its entirety.

FIELD OF THE INVENTION

The invention relates to methods for implanting cardiac support devices.

BACKGROUND OF THE INVENTION

Cardiac support devices are structures, sometimes referred to as jackets, that surround all or portions of a diseased heart. These devices are intended to treat chronic heart failure or other cardiac disease, which may be associated valvular dysfunction, by constraining expansion of the heart. They can be delivered and implanted using conventional cardiothoracic surgical techniques or minimally invasive surgical procedures. Devices of these types and associated delivery tools and methods are shown, for example, in the following U.S. patents and published applications, all of which are incorporated herein by reference in their entirety.

| Inventor Name | Patent/Publication No. |
| --- | --- |
| Alferness | 5,702,343 |
| Alferness et al. | 6,123,662 |
| Vanden Hoek et al. | 6,293,906 |
| Alferness et al. | 6,482,146 |
| Lau et al. | 6,702,732 |
| Cox et al. | 6,730,016 |
| Walsh et al. | 6,902,522 |
| Girard et al. | 6,951,534 |
| Walsh et al. | 2007/0208215 |
| Pignato et al. | 2007/0270654 |

Cardiac support devices (CSDs) can be implanted via conventional median sternotomy surgical procedures. In the course of an implantation using this procedure, the heart is typically lifted and the CSD is placed over the ventricles. It is then sutured along its base end to the epicardial fat near the atrioventricular (A-V) groove of the heart to prevent migration. Minimally invasive procedures can also be used to implant CSDs. CSDs configured for minimally invasive implantation can have elastomeric structures such as elastic bands incorporated into the base end of the CSD. The elastomeric band can attach the CSD to the heart (e.g., adjacent to the A-V groove).

CSDs have also been implanted using limited access techniques through a left minithoracotomy with fluoroscopic visualization. These techniques are attractive because they avoid median sternotomy, involve substantially less musculoskeletal trauma and can be performed with minimal heart manipulation. They are therefore associated with less hemodynamic stress.

Unfortunately, limited access approaches may not permit direct intraoperative visualization of the CSD. Fluoroscopic visualization can demonstrate the general shape of the heart and the location of the heart apex, but may not effectively show the location of other structures such as the A-V groove, the coronary sinus, the atrial appendages or the location of the pulmonary artery or right ventricular outflow tract. Although structures of the CSD may be radioopaque, and visible through fluoroscopic imaging, the locations of these CSD structures with respect to those of the heart can be difficult to assess. Accurate placement of the CSD can therefore be difficult to assess. There remains, therefore, a need for improved methods and structures for implanting CSDs. In particular, there is a need for improved methods and structures for accurately placing CSDs on the patients' hearts.

SUMMARY

The invention is an improved method for implanting a CSD on a patient's heart. One embodiment of the invention includes introducing contrast agent into a pericardial space surrounding the heart. The heart and contrast agent are imaged to provide a visual indication of the location of structures of the heart. The CSD is placed on the heart using the visual indications.

DETAILED DESCRIPTION OF THE PREFERRED EMBODIMENTS

Figure 1:
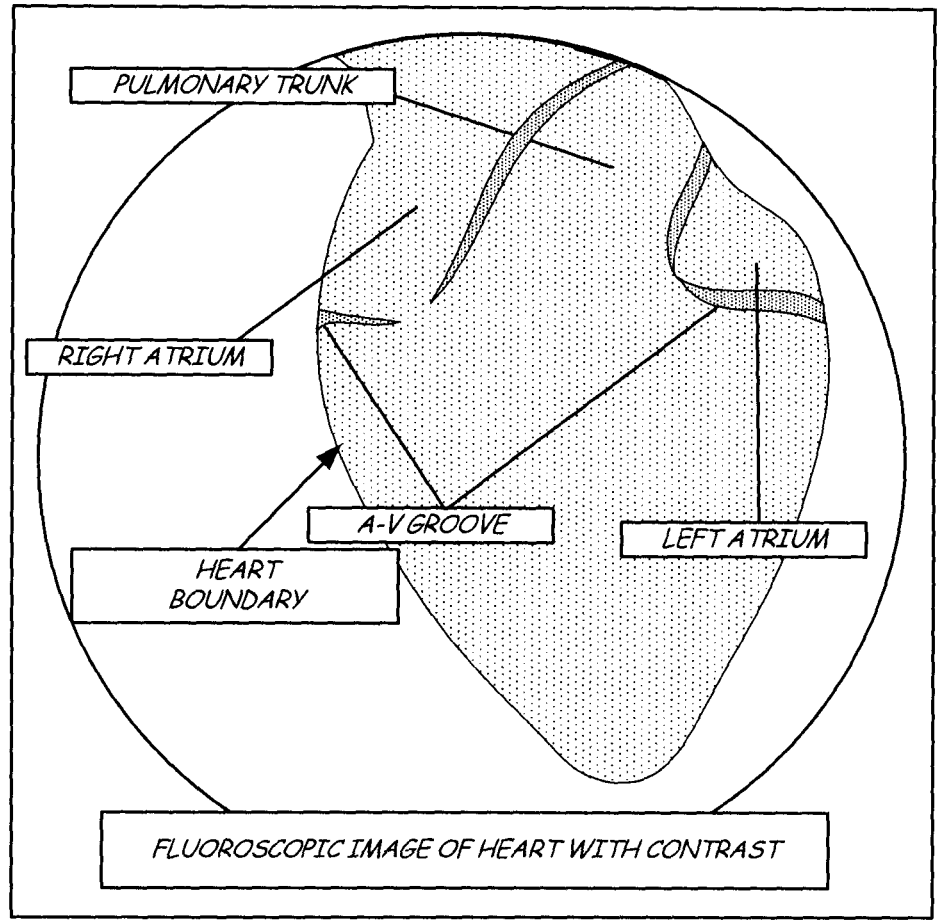
FIG. 1 is an illustration of a fluoroscopic image of a heart with contrast agent introduced into the pericardial space in accordance with one embodiment of the present invention.

When an amount of iodinated or other contrast agent solution (e.g., up to about 30 cc in one embodiment) is introduced into the intact pericardial space, the vigorous motion of the heart distributes the contrast rapidly throughout the pericardial space. The contrast collects in groves and fissures on the surface of the heart. This includes the crevice between the left atrial and right atrial appendages and adjacent structures, as well as the space between the aorta and superior vena cava, and the crevice adjacent to the coronary sinus. These contrast-filled crevices are located adjacent to the coronary sulcus and the atrioventricular (A-V) groove, and provide radiographic markers that effectively demonstrate where these structures on the heart are located. A CSD can then be placed accurately on the heart. Irrigating and evacuating the pericardial sack repeatedly with normal saline can remove the contrast at the end of a procedure, if so desired. Alternatively, the contrast can be left in place, and will drain from a chest tube over a period of time following surgery.

Any of a variety of methods can be used for introducing a contrast agent into the pericardial space. For example, tubular structures such as syringe needles and catheters can be inserted into the pericardial space through the pericardium. The contrast agent can then be delivered into the pericardial space through the tubular structure. One method utilizes a percutaneous puncture, either with a simple needle or a dedicated device configured to facilitate pericardial access, to instill iodinated contrast or other contrast agent into the intact pericardial space. An additional advantage of this procedure is that the contrast can help in detecting the presence of intrapericardial adhesions, which would preclude placement of a CSD by a limited access approach. Detecting adhesions prior to mini-thoracotomy would avoid the need to make an incision in a patient that could not undergo limited access implantation. A catheter placed in the intact pericardial space can be used to evacuate the contrast as well. If desired, irrigating and evacuating the pericardium through the catheter repeatedly with normal saline can provide more complete contrast removal.

In another embodiment, access is gained into the pericardial space via the vasculature. This can include access across the right atrial appendage as shown in Verrier, et al., Transatrial access to the normal pericardial space: a novel approach for diagnostic sampling, pericardiocentesis, and therapeutic interventions, Circulation, Nov. 24, 1998; 98(21):2331-3, or the ventricular wall as shown in Baek et al., Augmentation of intrapericardial nitric oxide level by a prolonged-release nitric oxide donor reduces luminal narrowing after porcine coronary angioplasty, Circulation, Jun. 11, 2002; 105(23): 2779-84.

Yet another embodiment utilizes a mini-thoracotomy placed in the appropriate intercostal space to allow visualization of the left ventricular apex. Through this incision, the pericardial sack is opened to permit limited access placement of the CSD. The pericardial edges of the apical opening are sutured to the thoracotomy margins. At this point, the patient is positioned so the apex of the heart is higher than the base. This can, for example, be done by positioning the bed in steep Trendelenberg and rolling it to the patient's right. Iodinated contrast solution, (e.g., approximately 30-60 cc), is introduced into the pericardial cavity. Even though the pericardium has been opened, contrast still pools and collects in naturally occurring crevices and grooves on the surface of the heart. Under fluoroscopy, this contrast agent provides anatomic landmarks that facilitate identification of the atrioventricular groove and accurate positioning of the CSD.

Figure 2:
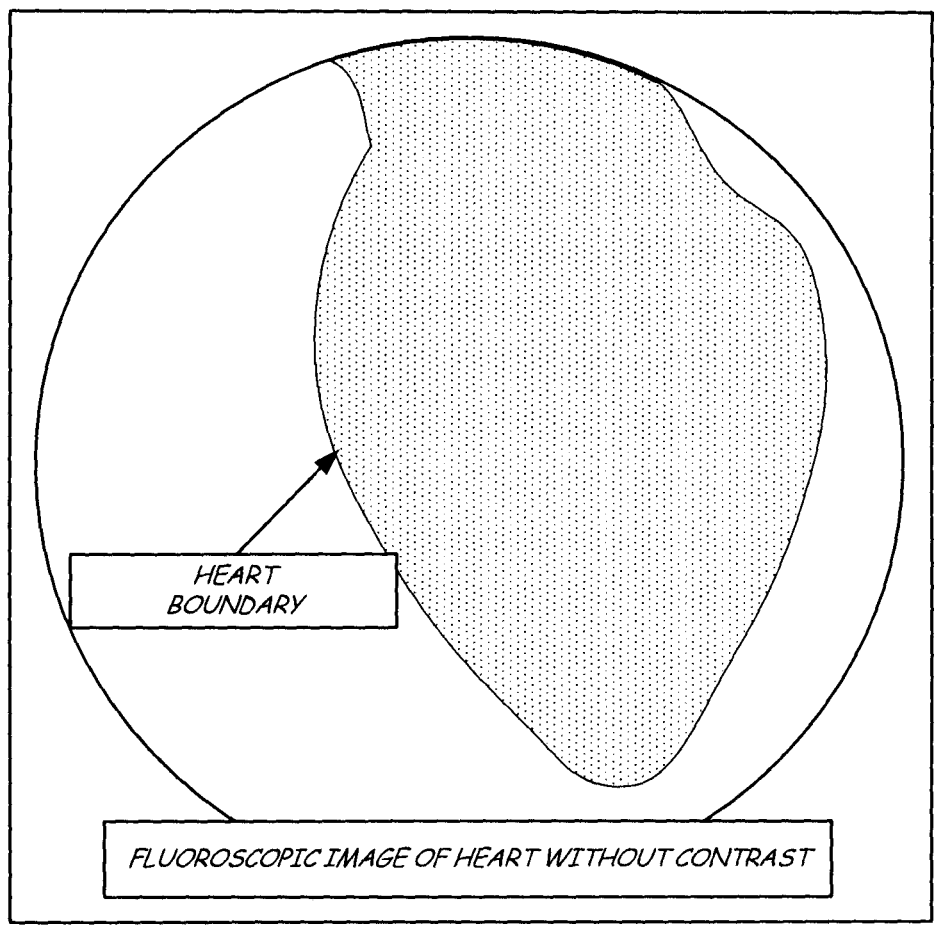
FIG. 2 is an illustration of a fluoroscopic image of a heart with the pericardial space free from contrast agent.

FIG. 1 is a fluoroscopic image of a heart with contrast agent in the pericardial space in accordance with the invention. The heart boundary, pulmonary trunk, right atrium, left atrium and A-V groove are visible in the image. For purposes of comparison, FIG. 2 is a fluoroscopic image of a heart without contrast agent. The heart boundary is apparent in FIG. 2, but specific structures such as the A-V groove are not visible.

Another embodiment of the invention for imaging the pericardial space in preparation for implanting a CSD through a minimally-invasive surgical opening includes the use of ultrasound imaging capabilities. In one example, transesophageal echocardiography is used to image the pericardial space. More precisely, an ultrasound contrast agent such as solutions with microbubbles, or alternatively, carbon dioxide gas insufflation of the pericardial space, can be used to identify anatomical landmarks near the atrioventricular groove. Another aspect of this approach may be the incorporation of ultrasound-opaque materials in the hemline of the CSD to facilitate imaging of the position of the hemline of the device with respect to structures on the heart such as the A-V groove during deployment on the heart. One approach would be to incorporate radioopaque gas into the silicone band within the hemline of the CSD. The band would then be visible under ultrasound imaging. Radioopaque markers on the CSD can also be used in connection with the imaging methods described above to accurately position CSDs on patents' hearts (i.e., by using the relative positions of the marked structures on the heart and the markers on the CSD to move the CSD into position).

Still other embodiments of the invention include the use of an air-tight collar at the opening in the pericardium to provide access to the pericardial space (i.e., there is a relatively high-vacuum seal between the collar and the pericardium). The collar can have an adhesive lip or other surface that secures the collar to the pericardium. In other embodiments the collar is sutured to the pericardium.

Although the embodiments of the invention described above use fluoroscopic and ultrasound imaging methods, other embodiments of the invention use other imaging methods such as, for example, MRI and CT. Other fluid (e.g., liquid or gas) contrast agents suitable for use with the selected imaging methodology can also be used.

In another embodiment of the invention contrast agent is introduced into the pericardial space after the CSD is positioned on the heart. The heart, contrast agent and CSD can then be imaged, and the resulting image used to assess the accuracy of CSD placement on the heart.

Figure 3:
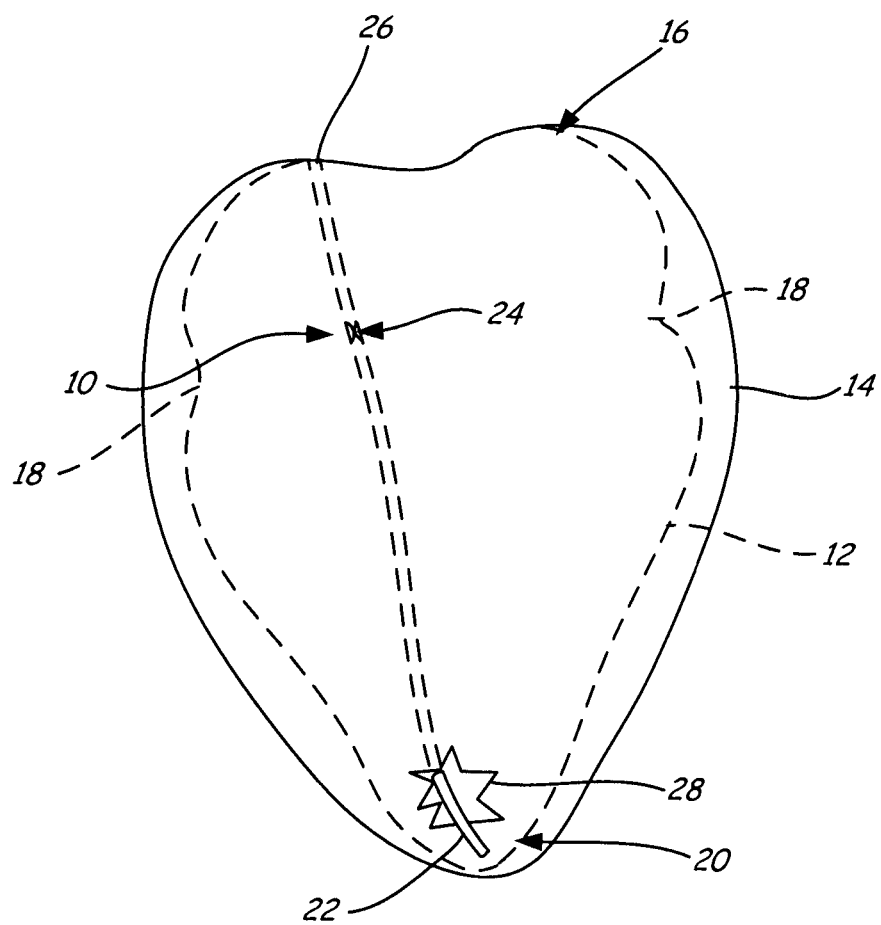
FIG. 3 is an illustration of an imaging tool in accordance with another embodiment of the invention inserted into the pericardial space surrounding a heart in accordance with another imaging method of the invention.

An alternative imaging location method and a tool 10 that can be used in connection with the method can be described with reference to FIG. 3, where a patient's heart 12 is shown in phantom surrounded by pericardium 14. As shown, the pericardium 14 is attached to the upper portions 16 of the heart 12 at locations near the great vessels (not shown), opposite the A-V groove 18 from the apex 20 of the heart. Tool 10 includes an elongated flexible member 22 having a radioopaque marker 24. Marker 24 is located a predetermined distance from the end 26 of the member 22. During use, the tool 10 is inserted into an opening such as 28 and advanced toward the intersection of the heart 12 and pericardium 14. The flexible member 22, which can be polymer, has sufficient rigidity to enable a surgeon or other clinician to advance the tool 10 into the pericardial space until the end 26 engages the intersection of the heart 12 and pericardium 14. The distance between the marker 24 and the end 26 of the member 22 are known to the surgeon. Since the distances between the intersection of the heart 12 and the pericardium 14 are generally known to the surgeon or clinician, the location of the marker 24 can be used as an indication of the location of the A-V groove 18. When imaged, the marker 24 therefore provides an indicia that can be used to accurately locate the base end of a CSD (not shown) on the patent's A-V groove 18. Tools 10 having markers 24 at different locations with respect to the end 26 of the member 22 can be used for patients having differently sized hearts, and for different locations of the heart of a given patient. Following the implantation of the CSD, the tools 10 can be removed. Air, carbon dioxide or other gases can be introduced (e.g., through the opening 28) to inflate the pericardial space and facilitate the accurate placement of the tools 10. Although not shown, more than one tool 10 can be inserted into the pericardial space to provide image markers. Other embodiments (not shown) also include more than one marker 24 on the member 22. In these embodiments the markers can be different from one another (e.g., in size or shape) so they can be distinguished from one another on images.

Although the present invention has been described with reference to preferred embodiments, those skilled in the art will recognize that changes can be made in form and detail without departing from the spirit and scope of the invention.

The invention claimed is:
1. A method for implanting a Cardiac Support Device (CSD) on a patient's heart, including:
   inserting one or more of a tool for visualizing locations within a pericardial space during the implantation of a CSD on a patient's heart, the tool comprising: an elongate flexible member having an end and one or more radioopaque markers on the elongate flexible member at a predetermined distance from the end into the pericardial space and positioning the end of the elongate flexible member at the intersection of the heart and pericardium;

imaging the heart and marker to provide a visual indication of the location of structures of the heart; and using the predetermined distance to determine the location of the intersection of the heart and the pericardium and using visual indications to position the CSD on the heart.

2. The method of claim 1, wherein imaging the heart includes providing visual indications of the location of the A-V groove and using the visual indication of the A-V groove to place the CSD on the heart.

3. The method of claim 1, further including removing the one or more tool for visualizing locations within a pericardial space.

4. The method of claim 1, further including applying a collar to the pericardium at an opening and causing the collar to form a vacuum seal with the pericardium.

\* \* \* \* \*